United States Patent
Kokin

(10) Patent No.: US 9,758,470 B2
(45) Date of Patent: Sep. 12, 2017

(54) BIS(PERFLUOROETHER CARBOXYLIC ACID ALKYL)AMINO ESTER AND METHOD FOR PRODUCING THE SAME

(71) Applicant: UNIMATEC CO., LTD., Tokyo (JP)

(72) Inventor: Keisuke Kokin, Ibaraki (JP)

(73) Assignee: Unimatec Co., Ltd., Tokyo (JP)

(*) Notice: Subject to any disclaimer, the term of this patent is extended or adjusted under 35 U.S.C. 154(b) by 0 days.

(21) Appl. No.: 14/910,961

(22) PCT Filed: Jul. 16, 2014

(86) PCT No.: PCT/JP2014/068874
§ 371 (c)(1),
(2) Date: Feb. 8, 2016

(87) PCT Pub. No.: WO2015/019809
PCT Pub. Date: Feb. 12, 2015

(65) Prior Publication Data
US 2016/0194275 A1  Jul. 7, 2016

(30) Foreign Application Priority Data
Aug. 9, 2013  (JP) ................................. 2013-166838

(51) Int. Cl.
C07C 219/06 (2006.01)
C07C 213/06 (2006.01)

(52) U.S. Cl.
CPC .......... *C07C 219/06* (2013.01); *C07C 213/06* (2013.01)

(58) Field of Classification Search
None
See application file for complete search history.

(56) References Cited

U.S. PATENT DOCUMENTS

| | | | |
|---|---|---|---|
| 5,606,098 A * | 2/1997 | Ryabinin | C07C 69/708 560/184 |
| 6,013,795 A | 1/2000 | Manzara et al. | |
| 6,348,266 B1 | 2/2002 | Liu et al. | |
| 2008/0221360 A1 | 9/2008 | Kokin et al. | |
| 2012/0041201 A1 | 2/2012 | Kokin et al. | |

FOREIGN PATENT DOCUMENTS

| | | |
|---|---|---|
| AU | 9026001 A | 4/2002 |
| CN | 1955166 A | 5/2007 |
| EP | 0693514 A1 | 1/1996 |
| JP | 62-270546 | 11/1987 |
| JP | 03-284642 | 12/1991 |
| JP | 10-036867 | 2/1998 |
| JP | 2002-514190 A | 5/2002 |
| JP | 2008-255035 | 10/2008 |
| JP | 2008-255042 | 10/2008 |
| JP | 2009-001709 | 1/2009 |
| JP | 2010-254736 A | 11/2010 |
| JP | 2011-202055 A1 | 10/2011 |
| JP | 2011-213837 | 10/2011 |
| JP | 2013-032455 | 2/2013 |
| WO | WO 02/26693 A1 | 4/2002 |
| WO | WO 2007-026513 A1 | 3/2007 |

OTHER PUBLICATIONS

English language machine generated translation of Ito (WO 02/26693, published on Apr. 4, 2002, p. 1-11).*
International Preliminary Report on Patentability and Written Opinion from corresponding PCT application No. PCT/JP2014/068874 dated Feb. 18, 2016 (6 pgs).
International Search Report from corresponding PCT application No. PCT/JP2014/068874 dated Sep. 30, 2014 (4 pgs).

* cited by examiner

*Primary Examiner* — Jafar Parsa
*Assistant Examiner* — Amy C Bonaparte
(74) *Attorney, Agent, or Firm* — Brinks Gilson & Lione

(57) ABSTRACT

A bis(perfluoroether carboxylic acid alkyl)amino ester represented by the general formula: $\{C_nF_{2n+1}O[CF(CF_3)CF_2O]_aCF(CF_3)COO(CH_2)_b\}_2NR$, wherein R is a hydrogen atom, an alkyl group having 1 to 12 carbon atoms, an aryl group, or an aralkyl group; preferably an alkyl group having 1 to 6 carbon atoms or an aryl group; n is an integer of 1 to 3; a is an integer of 0 to 20, preferably an integer of 1 to 6; and b is an integer of 1 to 12, preferably an integer of 1 to 4. The bis(perfluoroether carboxylic acid alkyl)amino ester having an amino group at the end of the ester group is produced by reacting a perfluoroether carboxylic acid fluoride compound of the formula: $C_nF_{2n+1}O[CF(CF_3)CF_2O]_aCF(CF_3)COF$ and a bis(hydroxyalkyl)amine compound of the formula: $HO(CH_2)_bNR(CH_2)_bOH$ at a molar ratio of 2:1 in the presence of an alkali metal fluoride.

5 Claims, No Drawings

BIS(PERFLUOROETHER CARBOXYLIC ACID ALKYL)AMINO ESTER AND METHOD FOR PRODUCING THE SAME

RELATED APPLICATION

This application is a 35 U.S.C. §371 national phase filing of International Patent Application No. PCT/JP2014/068874, filed Jul. 16, 2014, which claims priority under 35 U.S.C. §119 to Japanese Patent Application No. 2013-166838, filed Aug. 9, 2013, the entire disclosure of which is hereby expressly incorporated by reference.

TECHNICAL FIELD

The present invention relates to a bis(perfluoroether carboxylic acid alkyl)amino ester and a method for producing the same. More particularly, the present invention relates to a bis(perfluoroether carboxylic acid alkyl)amino ester, to which flexibility in the molecular chain is imparted by an ether linkage in the molecule, and which is effectively used as a synthetic raw material, etc.; and the present invention also relates to a method for producing the same.

BACKGROUND ART

Heretofore, the present applicant has proposed various fluoroethers or fluorine-containing polyether carboxylic acid amides having a terminal alkylamino group, to which flexibility in the molecular chain is imparted by an ether linkage in the molecule, (see Patent Documents 1 to 7). Further, the present applicant has also proposed fluorine-containing acid fluoride compounds having COOH, CONH$_2$, or the like at the molecular end (see Patent Document 8).

However, there has been no finding on fluorine-containing ether carboxylic acid esters having an amino group at the end of the ester group.

PRIOR ART DOCUMENT

Patent Document

Patent Document 1: WO 2007/026513
Patent Document 2: JP-A-2008-255042
Patent Document 3: JP-A-2009-1709
Patent Document 4: JP-A-2010-254736
Patent Document 5: JP-A-2011-202055
Patent Document 6: JP-A-2011-213837
Patent Document 7: JP-A-2013-32455
Patent Document 8: JP-A-2008-255035
Patent Document 9: JP-A-3-284642
Patent Document 10: JP-A-62-270546

OUTLINE OF THE INVENTION

Problem to be Solved by the Invention

An object of the present invention is to provide a bis(perfluoroether carboxylic acid alkyl)ester having amino groups at both ends of the ester group, and a method for producing the same.

Means for Solving the Problem

The above present invention provides a bis(perfluoroether carboxylic acid alkyl)amino ester represented by the general formula:

$$\{C_nF_{2n+1}O[CF(CF_3)CF_2O]_aCF(CF_3)COO(CH_2)_b\}_2NR \quad [\text{I}]$$

wherein R is a hydrogen atom, an alkyl group having 1 to 12 carbon atoms, an aryl group, or an aralkyl group; preferably an alkyl group having 1 to 6 carbon atoms or an aryl group; n is an integer of 1 to 3; a is an integer of 0 to 20, preferably an integer of 1 to 6; and b is an integer of 1 to 12, preferably an integer of 1 to 4.

Such a bis(perfluoroether carboxylic acid alkyl)amino ester is produced by reacting a perfluoroether carboxylic acid fluoride compound represented by the general formula:

$$C_nF_{2n+1}O[CF(CF_3)CF_2O]_aCF(CF_3)COF \quad [\text{II}]$$

wherein n is an integer of 1 to 3, and a is an integer of 0 to 20, preferably an integer of 1 to 6; and a bis(hydroxyalkyl)amine compound represented by the general formula:

$$HO(CH_2)_bNR(CH_2)_bOH \quad [\text{III}]$$

wherein R is a hydrogen atom, an alkyl group having 1 to 12 carbon atoms, an aryl group, or an aralkyl group, preferably an alkyl group having 1 to 6 carbon atoms or an aryl group; and b is an integer of 1 to 12, preferably an integer of 1 to 4; in the presence of an alkali metal fluoride.

Effect of the Invention

The present invention provides a bis(perfluoroether carboxylic acid alkyl)amino ester, to which flexibility in the molecular chain is imparted by an ether linkage in the molecule, and which is effectively used as a synthetic intermediate for various substances, or which itself is cured to form a fluorine-containing polymer having flexibility.

EMBODIMENTS FOR CARRYING OUT THE INVENTION

The bis(perfluoroether carboxylic acid alkyl)amino ester [I] of the present invention is produced by reacting a perfluoroether carboxylic acid fluoride compound [II] and a bis(hydroxyalkyl)amine compound [III] in the presence of an alkali metal fluoride.

The perfluoroether carboxylic acid fluoride compound [II] is represented by the general formula:

$$C_nF_{2n+1}O[CF(CF_3)CF_2O]_aCF(CF_3)COF \quad [\text{II}]$$

n: 1 to 3
a: 0 to 20, preferably 1 to 6
each of which is a known compound.

Specifically, Patent Document 9 discloses a compound wherein n is 1 or 2, and Patent Document 10 discloses a compound wherein n is 3. Moreover, these patent documents indicate that a is an integer of 0 or 1 or more, and specifically disclose a compound wherein a=0, which is a dimer of hexafluoropropene oxide [HFPO], a compound wherein a=1, which is a trimer of HFPO, a compound wherein a=2, which is a tetramer of HFPO, and the like, that is a synthetic raw material thereof.

Since these perfluoroether carboxylic acid fluoride compounds are easily reacted with water, the alkali metal fluoride used in the reaction is preferably calcined immediately before use to adjust the moisture content to 0.1 wt. % or less.

Examples of the bis(hydroxyalkyl)amine compound [III], which react with such a perfluoroether carboxylic acid fluoride compound [II], preferably a bis(ω-hydroxyalkyl) amine compound, include diethanolamine, N-methyldiethanolamine, N-ethyldiethanolamine, N-propyldiethanolamine, bis(3-hydroxypropyl)amine, N-methylbis(3-hydroxypropyl)

amine, N-ethylbis(3-hydroxypropyl)amine, N-propylbis(3-hydroxypropyl)amine, N-phenyldiethanolamine, N-p-toluyldiethanolamine, N-phenylbis(3-hydroxypropyl)amine, N-p-toluylbis(3-hydroxypropyl)amine, N-benzyldiethanolamine, and the like.

These compounds [II] and [III] are stoichiometrically used at a molar ratio of 2:1; however, in practice, the compound [III] is generally used at a small excess molar ratio relative to the compound [II].

Moreover, examples of the alkali metal fluoride, which acts as a scavenger for hydrogen fluoride by-produced in the reaction, include sodium fluoride, potassium fluoride, cesium fluoride, rubidium fluoride, acidic sodium fluoride, acidic potassium fluoride, and the like. Sodium fluoride is suitably used in terms of price, availability, and handling during the reaction. The alkali metal fluoride is used in an about 2 times molar amount that of the compound [II].

It is preferable to use a solvent in the reaction. Particularly preferred solvents are fluorine-containing solvents, such as HCFC-225 (dichloropentafluoropropane), HFE-449 (methoxy nonafluorobutane), HFE-569 (ethoxy nonafluorobutane), and 1,3-bis(trifluoromethyl)benzene. In practice, commercial products, such as AE-3000 and AK-225 (produced by Asahi Glass Co., Ltd.), Novec HFE (produced by Sumitomo 3M Co., Ltd.), and Vertrel XF (produced by Du Pont-Mitsui Fluorochemicals Co., Ltd.), are suitably used.

Although the reaction temperature is not particularly limited, the reaction is preferably performed at a low temperature, particularly preferably at about 0 to 10° C., in terms of productivity.

After completion of the reaction, the alkali metal fluoride forming a complex with hydrogen fluoride by-produced in the reaction is removed by filtration or other means. The removing method is not particularly limited, and can be any filtration method selected from vacuum filtration, pressure filtration, centrifugal filtration, and the like.

Thereafter, washing with an alkali metal hydroxide aqueous solution having a dilute concentration is performed to remove hydrogen fluoride binding to amino groups present in the reaction mixture liquid. The alkali metal hydroxide is preferably sodium hydroxide or potassium hydroxide. The concentration of its queous solution is preferably more dilute; in particular, an aqueous solution having a concentration of about 1 to 5 wt. % is preferably used. Washing with this alkali metal hydroxide aqueous solution is preferably performed at a low temperature, particularly preferably at about 0 to 5° C., because hydrolysis progresses at a high temperature.

After washing with the alkali aqueous solution, the fluorine-containing solvent is removed under reduced pressure. The removing method is suitably selected from a distillation device, an evaporator, a thin film dryer, etc., depending on the entire volume. The obtained reaction product is purified by removing impurities by molecular distillation or the like. Thus, the target product, i.e., a bis(perfluoroether carboxylic acid alkyl)amino ester, can be obtained.

EXAMPLES

The following describes the present invention with reference to Examples.

Example 1

A 2-L flask equipped with stirring blades, a thermometer, a dropping funnel, and a condenser was sealed with nitrogen gas. Then, 600 g of fluorine-containing solvent (Novec HFE, produced by Sumitomo 3M Co., Ltd.), 23.2 g (195 mmol) of N-methyldiethanolamine dried over potassium hydroxide, and 33.6 g (800 mmol) of NaF calcined at 230° C. were charged therein, and the mixture was cooled to −10° C. in a salt/ice bath. Subsequently, 200 g (purity: 99.5%; 400 mmol) of 2-[1,1,2,3,3,3-hexafluoro-2-(heptafluoropropoxy)propoxy]-2,3,3,3-tetrafluoropropanoyl fluoride of the formula: $CF_3CF_2CF_2O[CF(CF_3)CF_2O]CF(CF_3)COF$ was slowly added dropwise.

After completion of dropping, the mixture was stirred at 0° C. or less for 2 hours. Then, NaF in the reaction mixture was removed by pressure filtration. After the reaction mixture was cooled to 10° C. or less, 3,000 g of 1 wt. % KOH aqueous solution was added, and the mixture was stirred and washed for 5 minutes. The organic phase was collected, and the fluorine-containing solvent was removed under reduced pressure using an evaporator, thereby obtaining a high-purity yellow residue. The residue was supplied in a molecular distillation device adjusted to an internal temperature of 200° C., thereby obtaining 180.5 g (yield: 86.2%) of N-methylbis(perfluoroether carboxylic acid alkyl)amino ester compound as a nonvolatile component.

$$\{C_3F_7O[CF(CF_3)CF_2O]CF(CF_3)COO(CH_2)_2\}_2NCH_3$$

| $\delta$ = −79.7 to −86.8: | —$CF_2$O— | (m, 8F) |
|---|---|---|
| −82.0: | —$\underline{CF}(CF_3)$COO— | (s, 6F) |
| −83.1: | —CF($\underline{CF_3}$)$CF_2$O— | (s, 6F) |
| −83.9: | $CF_3\underline{CF_2}$— | (s, 6F) |
| −130.8: | $\overline{CF_3CF_2}CF_2$O— | (s, 4F) |
| −132.8: | —$\underline{CF}(CF_3)$COO— | (t, 2F) |
| −145.0 to −146.2: | —$\underline{CF}(CF_3)CF_2$O— | (m, 2F) |

$^1$H-NMR (acetone-d6, TMS standard, ppm):

| $\delta$ = 4.31: | —OC$\underline{H_2}$— | (t, 4H) |
|---|---|---|
| 2.51: | —C$\underline{H_2}$N— | (m, 4H) |
| 2.28: | C$\underline{H_3}$— | (s, 3H) |
| IR: 1791 cm$^{-1}$ —C=O vibration | | |

Example 2

In Example 1, 35.3 g (195 mmol) of N-phenyldiethanolamine was used in place of N-methyldiethanolamine, thereby obtaining 198.8 g (yield: 89.7%) of N-phenylbis(perfluoroether carboxylic acid alkyl)amino ester compound as a nonvolatile component.

$$\{C_3F_7O[CF(CF_3)CF_2O]CF(CF_3)COO(CH_2)_2\}_2NC_6H_5$$

| $\delta$ = −80.0 to −85.6: | —$CF_2$O— | (m, 10F) |
|---|---|---|
| −82.4: | —$\underline{CF}(CF_3)$COO— | (s, 3F) |
| −83.0: | —CF($\underline{CF_3}$)$CF_2$O— | (s, 3F) |
| −83.2: | $CF_3\underline{CF_2}$— | (s, 3F) |
| −131.4: | $\overline{CF_3CF_2}CF_2$O— | (s, 2F) |
| −133.1: | —$\underline{CF}(CF_3)$COO— | (t, 2F) |
| −145.0 to −145.9: | —$\underline{CF}(CF_3)CF_2$O— | (m, 4F) |

$^1$H-NMR (acetone-d6, TMS standard, ppm):

| δ = 7.18 to 6.62: | aromatic | (m, 5H) |
|---|---|---|
| 4.29: | —OCH$_2$— | (m, 4H) |
| 3.33; | —C$\underline{H_2}$N— | (m, 4H) |
| IR: 1792 cm$^{-1}$ —C=O vibration | | |

Example 3

In Example 1, the amount of fluorine-containing solvent was changed to 1,500 g, and 544 g (400 mmol) of perfluoroether carboxylic acid fluoride compound represented by the following formula:

$$C_3F_7O[CF(CF_3)CF_2O]_aCF(CF_3)COF$$

a: 8.2 (number average degree of polymerization), Mn: 1,361 was used, thereby obtaining 498 g (yield: 91.3%) of N-methylbis(perfluoroether carboxylic acid alkyl)amino ester compound as a nonvolatile component.

$$\{C_3F_7O[CF(CF_3)CF_2O]_aCF(CF_3)COO(CH_2)_2\}_2NCH_3$$

$^{19}$F-NMR (acetone-d6, CFCl$_3$ standard, ppm):

| δ = −80.2 to −85.8: | —CF$_2$O— | (m) |
|---|---|---|
| −82.2: | —C$\underline{F}$(CF$_3$)COO— | (s) |
| −83.1: | —CF(C$\underline{F_3}$)CF$_2$O— | (s) |
| −83.4: | CF$_3$C$\underline{F_2}$— | (s) |
| −131.2: | C$\underline{F_3}$CF$_2$CF$_2$O— | (s) |
| −133.0: | —CF(C$\underline{F_3}$)COO— | (t) |
| −145.1 to −146.2: | —C$\underline{F}$(CF$_3$)CF$_2$O— | (m) |

$^1$H-NMR (acetone-d6, TMS standard, ppm):

| δ = 4.30: | —OCH$_2$— | (t, 4H) |
|---|---|---|
| 2.52: | —C$\underline{H_2}$N— | (m, 4H) |
| 2.27: | CH$_3$— | (s, 3H) |
| IR: 1793 cm$^{-1}$ —C=O vibration | | |

The invention claimed is:

1. A bis(perfluoroether carboxylic acid alkyl)amino ester of the general formula:

$$\{C_nF_{2n+1}O[CF(CF_3)CF_2O]_aCF(CF_3)COO(CH_2)_b\}_2NR \quad [I]$$

wherein R is a hydrogen atom, an alkyl group having 1 to 12 carbon atoms, or a phenyl group; n is an integer of 1 to 3; a is an integer of 0 to 20; and b is an integer of 1 to 12.

2. A method for producing the bis(perfluoroether carboxylic acid alkyl)amino ester according to claim 1, the method comprising reacting a perfluoroether carboxylic acid fluoride compound of the general formula:

$$C_nF_{2n+1}O[CF(CF_3)CF_2O]_aCF(CF_3)COF \quad [II]$$

wherein n is an integer of 1 to 3, and a is an integer of 0 to 20; and a bis(hydroxyalkyl)amine compound of the general formula:

$$HO(CH_2)_bNR(CH_2)_bOH \quad [III]$$

wherein R is a hydrogen atom, an alkyl group having 1 to 12 carbon atoms, or a phenyl group; and b is an integer of 1 to 12; in the presence of an alkali metal fluoride.

3. The method for producing the bis(perfluoroether carboxylic acid alkyl)amino ester according to claim 2, wherein the compounds [II] and [III] are used at a molar ratio of 2:1.

4. The method for producing the bis(perfluoroether carboxylic acid alkyl)amino ester according to claim 2, wherein alkali washing is performed after the reaction of claim 2 is performed.

5. The method for producing the bis(perfluoroether carboxylic acid alkyl)amino ester according to claim 2, wherein alkali washing is performed after the reaction of claim 3 is performed.

* * * * *